United States Patent
Zagorchev

(10) Patent No.: US 12,198,272 B2
(45) Date of Patent: Jan. 14, 2025

(54) PATIENT-SPECIFIC CORTICAL SURFACE TESSELLATION INTO DIPOLE PATCHES

(71) Applicant: KONINKLIJKE PHILIPS N.V., Eindhoven (NL)

(72) Inventor: Lyubomir Georgiev Zagorchev, Burlington, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 616 days.

(21) Appl. No.: 17/428,437

(22) PCT Filed: Feb. 7, 2020

(86) PCT No.: PCT/EP2020/053208
§ 371 (c)(1),
(2) Date: Aug. 4, 2021

(87) PCT Pub. No.: WO2020/161338
PCT Pub. Date: Aug. 13, 2020

(65) Prior Publication Data
US 2022/0108525 A1 Apr. 7, 2022

Related U.S. Application Data

(60) Provisional application No. 62/802,275, filed on Feb. 7, 2019.

(51) Int. Cl.
*G06T 17/20* (2006.01)
*A61B 5/00* (2006.01)
(Continued)

(52) U.S. Cl.
CPC ............ *G06T 17/20* (2013.01); *A61B 5/291* (2021.01); *A61B 5/6814* (2013.01); *G06T 7/10* (2017.01);
(Continued)

(58) Field of Classification Search
CPC . G06T 17/20; G06T 7/10; G06T 2207/10088; G06T 2207/30016; G06T 2210/41; A61B 5/6814; A61B 5/291
See application file for complete search history.

(56) References Cited

U.S. PATENT DOCUMENTS 7,421,136 B2 * 9/2008 Sirohey ............... H04N 19/593
375/E7.184
8,031,919 B2 10/2011 Eskildsen
(Continued)

FOREIGN PATENT DOCUMENTS

CA 1606870 A1 11/2006
CN 104605845 A 5/2015
(Continued)

OTHER PUBLICATIONS

Hammond David K et al: "Cortical Graph Smoothing: A Novel Method for Exploiting DWI-Derived Anatomical Brain Connectivity to Improve EEG Source Estimation" IEEE Transactions on Medical Imaging, IEEE service center, vol. 32, No. 10, Oct. 1, 2013 (Oct. 1, 2013), pp. 1952-1963, D1: XP-011528135. (Year: 2013).*
(Continued)

*Primary Examiner* — John J Lee
(74) *Attorney, Agent, or Firm* — Sherry Austin

(57) ABSTRACT

A method (26) that tessellates a cortical surface of a brain with a plurality of dipole patches, wherein a quantity of the plurality of dipole patches is variable and dependent upon a head size.

20 Claims, 6 Drawing Sheets

(51) Int. Cl.
*A61B 5/291* (2021.01)
*G06T 7/10* (2017.01)
(52) U.S. Cl.
CPC ............... *G06T 2207/10088* (2013.01); *G06T 2207/30016* (2013.01); *G06T 2210/41* (2013.01)

(56) References Cited

U.S. PATENT DOCUMENTS

| | | | |
|---|---|---|---|
| 10,149,618 | B1 | 12/2018 | Tandon |
| 10,959,656 | B2 | 3/2021 | Kanayama |
| 2016/0081577 | A1 | 3/2016 | Sridhar et al. |
| 2017/0332933 | A1* | 11/2017 | Krishnaswamy ...... A61B 5/336 |
| 2018/0276822 | A1 | 9/2018 | Liu et al. |

FOREIGN PATENT DOCUMENTS

| | | | |
|---|---|---|---|
| CN | 105395194 | A | 3/2016 |
| CN | 107430690 | A | 12/2017 |
| CN | 107818567 | A | 3/2018 |
| WO | WO2016073985 | A1 | 5/2016 |
| WO | WO-2020109188 | A1 * | 6/2020 |

OTHER PUBLICATIONS

Acar et al: "Patch-Based Cortical Source Imaging in Epilepsy"; Conf Proc IEEE Eng Med Biol Soc, 2009, pp. 1-11.
Hyde et al: "Voxel-Based Dipole Orientation Constraints for Distributed Current Estimation"; IEEE Transactions on Biomedical Engineering, vol. 61, No. 7, Jul. 2014, pp. 2028-2040.
Ding et al: "Three-Dimensional Imaging of Complex Neural Activation in Humans From EEG"; IEEE Transactions on Biomedical Engineering, vol. 56, No. 8, Aug. 2009, pp. 1980-1988.
Hammond et al: "Cortical Graph Smoothing: a Novel Method for Exploiting DWI-Derived Anatomical Brain Connectivity to Improve EEG Source Estimation"; IEEE Transactions on Medical Imaging, vol. 32, No. 10, Oct. 2013, pp. 1952.
PCT/EP2020/053208 ISR & WO, Apr. 9, 2020, 16 Pages.
Knapp: Mesh Decimation Using VTK; Institute of Computer Raphics and Algorithms, Vienna University of Technology, 2002, 8 Page Document.
Kruggel: Robust Parametrization of Brain Surface Meshes; Science Direct, Medical Image Analysis 12 (2008) pp. 291-299.
Kuo et al: "EEG Source Imagin GOF Epileptic Activity at Seizure Onset"; Epilepsy Research, 46 (2018), pp. 160-171.
Liao et al:"SPARSE Imaging of Cortical Electrical Current Densities via Wavelet Transforms"; Phys. Med. Biol. 57 (2012), pp. 6881-6901.
Lorensen et al: "Marching Cubes: a High Resolution 3D Surface Construction Algorithm"; Computer Graphics, vol. 21, No. 4, Jul. 1987, pp. 163-169.
Nielson et al: "The Asymptotic Decider: Resolving the Ambiguity in Marching Cubes"; IEEE, 1991, pp. 83-91.
Weese et al: "Shape-Constained Deformable Models and Applications in Medical Imaging"; Springer Link, Shape Analysis in Medical Image Analysis, pp. 151-184, 2014.
Wenzel et al: "Rapid Fully Automatic Segmentation of Subcortical Brain Structures by Shape-Constrained Surface Adaptation"; Philips Research Submitted to Medical Image Analysis, Feb. 23, 2018.
Zagorchev et al: "Evaluation of Traumatic Brain Injury Patients Using a Shape-Constrained Deformable Model"; MBIA' 11:Proceedings of the First International Conference on Multimodal Brain Image Analysis, Sep. 2011 pp. 118-125 (Abstract).
Zagorchev et al: "Manual Annotation, 3-D Shape Reconstruciton, and Traumatic Brain Injury Analysis"; MBIA 2011: Multimodal Brain Image Analysis, pp. 52-59 (Abstract).
Hammond D. K. et al., "Cortical Graph Smoothing: A Novel Method for Exploiting DWI-Derived Anatomical Brain Connectivity to Improve EEG Source Estimation", IEEE Transactions on Medical Imaging, vol. 32, No. 10, pp. 1952-1963, Oct. 2013.
Jinj L.I. et al., "Study on the Effects of Skull Holes to the Scalp EEG by Means of Finite Difference Method", Chinese Journal of Biomedical Engineering, vol. 26, No. 5, Oct. 2007.

* cited by examiner

PATIENT-SPECIFIC CORTICAL SURFACE TESSELLATION INTO DIPOLE PATCHES

CROSS-REFERENCE TO PRIOR APPLICATIONS

This application is the U.S. National Phase application under 35 U.S.C. § 371 of International Application No. PCT/EP2020/053209, filed on Feb. 7, 2020, which claims the benefit of U.S. Provisional Patent Application No. 62/802,275, filed on Feb. 7, 2019. These applications are hereby incorporated by reference herein.

FIELD OF THE INVENTION

The present invention is generally related to electrical source imaging, and in particular, formulating a forward model used in electrical source imaging.

BACKGROUND OF THE INVENTION

Epilepsy is a public health problem that affects almost 3 million individuals in the US alone. Surgery is the most effective treatment for medically intractable epilepsy and can be curative if the seizure focus can be localized. Minimally invasive interventions to remove a seizure focus have significant advantages over open head surgery, including resulting in greater preservation of tissue and having better overall functional outcomes. Both minimally invasive ablations and open head surgeries require the use of high-resolution, structural magnetic resonance imaging (MRI) to identify and visualize the seizure focus. Electrical source imaging (ESI) is a neuroimaging technique. ESI from electroencephalography (EEG) electrodes positioned on the scalp can localize the seizure focus on the cortical surface. Using scalp potentials as measured by electroencephalography (EEG) electrodes, ESI estimates the location of sources in the brain responsible for those scalp potentials. The propagation of electrical activity is governed by a partial differential equation. In ESI, this partial differential equation is used to formulate a forward model and its inverse solution. The forward model is formulated to describe how electrical activity generated by a cortical source.

The accuracy of the forward model depends on individual head geometry and the electrical conductivity properties of head tissue types including, gray matter, white matter, cerebrospinal fluid, scalp, skull, air cavities, and eyeballs. In formulating the forward model, the gray matter is further tessellated into surface patches to define dipole locations and orientations. Tessellating this gray matter can be difficult. The human cerebral cortex is wrinkled in order to contain more brain tissue within the closed skull. The grooves that make these wrinkles are called sulci, and the ridges between them are known as gyri. Thus, the surface representation of the cortical gray matter is deeply convoluted. The goal of the dipole tessellation is to parcellate the cortical surface into patches that may be responsible for abnormal electrical discharges. The dipole patches are represented with patch centers, patch normals, and surface triangles that belong to the patch. These properties are used as boundary conditions in the forward model. Precise representation of the geometry at hand is very important for defining the propagation of electrical activity from the cortex to the scalp.

Current dipole tessellation methods limit the number of dipoles to a predefined constant, which results in dipole patches that cover gyri and sulci simultaneously. As a result, the dipole patch normals are calculated as an average that does not represent the cortical geometry.

SUMMARY OF THE INVENTION

One object of the present invention is to improve upon current methods of cortical surface tessellation. To better address such concerns, in a first aspect of the invention, a method that tessellates a cortical surface with a plurality of dipole patches, wherein a quantity of the plurality of dipole patches is variable and dependent upon a head size. Using the method of cortical surface tessellation, the accuracy of the forward model may be improved, resulting in improvements in electrical source imaging and, more generally, a more accurate and patient specific diagnosis and outcomes.

In one embodiment, the cortical surface consists of a gray matter surface of the cortex. Electroencephalograph source localization is generally considered an underdetermined problem because of the many (e.g., infinite) possible inverse configurations that can result in the same scalp potential. One mechanism to place constraints on the solution is to constrain the cortical surface to gray matter.

In one embodiment, the method further comprises receiving a volumetric bitmask of the cortex, wherein each voxel of a plurality of voxels is labeled according to a tissue type; providing a triangular mesh representation of the segmented cortical surface based on the volumetric bitmask; providing a high resolution triangular mesh containing triangles with uniform edge length by re-meshing the triangular mesh representation; and providing a simplified triangular mesh representation by applying a topology preserving, mesh decimation algorithm to the high resolution triangular mesh representation. The dipole patches may be obtained by using a simplified mesh as a template. The mesh decimation algorithm maintains the cortical folding and geometry, providing for a more realistic model and hence improved accuracy for achieving source localization.

In one embodiment, the method further comprises obtaining the plurality of dipole patches by: associating each triangle from the high resolution triangular mesh representation to its closest triangle from the simplified triangular mesh representation, wherein a final quantity of the plurality of dipole patches equals a quantity of triangles of the simplified triangular mesh representation. By doing so, the risk of combining sulci and gyri is eliminated or mitigated, since the number of dipole patches is not limited to a predefined constant.

In one embodiment, each of the plurality of dipole patches comprises properties that are used as boundary conditions in a forward model used in electrical source imaging. The accuracy of the forward model depends on individual head geometry and electrical conductivity properties of head tissue types including, gray matter, white matter, etc., with improvements in the determinations of these properties aiding in achieving more accurate electrical source imaging results.

In one embodiment, each dipole patch center is determined by: determining a center of mass of all triangles of the high resolution triangular mesh representation associated with a particular one of the closest triangles, wherein a center of a high resolution mesh triangle closest to the center of mass is selected as the dipole patch center; wherein a normal of the dipole patch corresponds to an average of all normals of the triangles of the high resolution triangular mesh representation. By doing so, a more accurate depiction of the dipole patches may be provided.

These and other aspects of the invention will be apparent from and elucidated with reference to the embodiment(s) described hereinafter.

BRIEF DESCRIPTION OF THE DRAWINGS

Many aspects of the invention can be better understood with reference to the following drawings, which are diagrammatic. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION OF EMBODIMENTS

Figure 1:
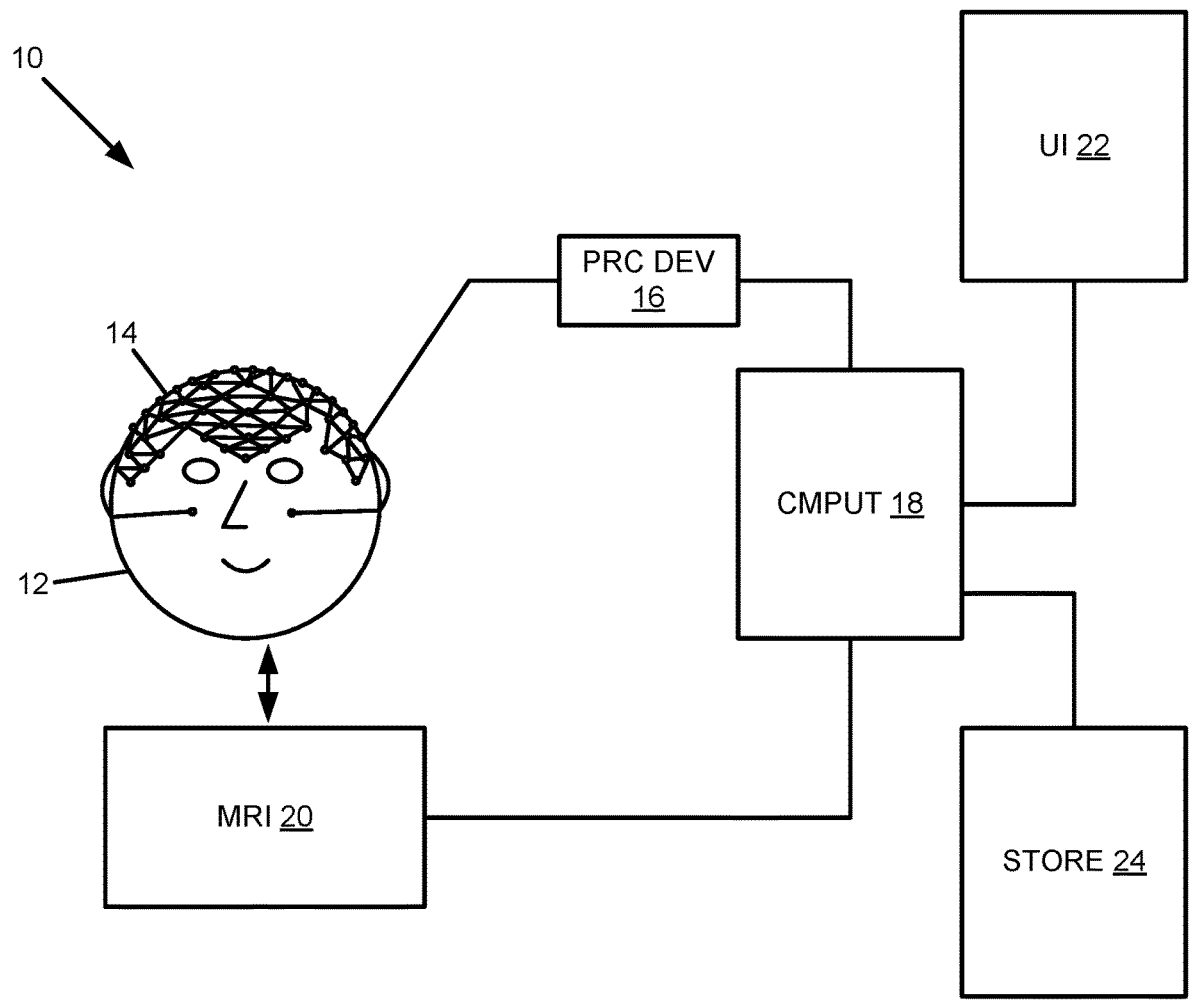
FIG. 1 is a schematic diagram that illustrates an example environment in which a cortical surface tessellation method is implemented, in accordance with an embodiment of the invention.

Disclosed herein are certain embodiments of a cortical surface tessellation method (and associated apparatus and system) that provides for (an automatic) tessellation of a cortical surface into dipole patches necessary for accurate electrical source imaging (ESI) localization. Certain embodiments of a cortical surface tessellation method provide for an accurate representation of the propagation of electrical activity from the cortex to the scalp by virtue of having dipole patches with normals perpendicular to all triangles in the patch, and the number of patches depending on the head size.

Digressing briefly, current dipole tessellation methods limit the number of dipole patches to a predefined constant, which results in dipole patches that cover gyri and sulci simultaneously. In other words, one or more of the dipole patches may each span several gyri and sulci, resulting in incorrect dipole normals. In contrast, certain embodiments of a cortical surface tessellation method address this and other issues and improve electrical source imaging by tessellating the cortical gray matter in dipole patches and calculating more accurate normals associated with those dipole patches.

Having summarized certain features of a cortical surface tessellation method of the present disclosure, reference will now be made in detail to the description of a cortical surface tessellation method as illustrated in the drawings. While a cortical surface tessellation method will be described in connection with these drawings, there is no intent to limit it to the embodiment or embodiments disclosed herein. Further, although the description identifies or describes specifics of one or more embodiments, such specifics are not necessarily part of every embodiment, nor are all of any various stated advantages necessarily associated with a single embodiment. On the contrary, the intent is to cover all alternatives, modifications and equivalents included within the principles and scope of the disclosure as defined by the appended claims. For instance, two or more embodiments may be interchanged or combined in any combination. Further, it should be appreciated in the context of the present disclosure that the claims are not necessarily limited to the particular embodiments set out in the description.

FIG. 1 is a schematic diagram that illustrates an example environment 10 in which a cortical surface tessellation method is implemented. The environment 10 may include a clinical setting at a hospital or physician's office or an educational or research facility. The environment 10 includes a subject 12 that is fitted with an encephalography (EEG) net 14 comprising a plurality of electrodes/sensors (hereinafter, referred to as electrodes, though used interchangeably herein with sensors). The EEG net 14 may include 32, 64, 128, or 256 EEG electrodes and hence EEG electrode channels. The EEG net 14 is coupled to a processing device 16. The processing device 16 comprises an amplifier that is configured to filter, measure, and sample the EEG signals acquired by the EEG net 14, and then transfer the digitized samples to the computing device 18 for use in head modeling (e.g., solving the forward and inverse problems) and, generally, estimating cortical activity. Electrical source imaging (ESI) from the electrodes of the EEG net 14 positioned on the scalp of the subject 12 may be used to localize the seizure focus on the cortical surface. In other words, signals to/from the EEG electrodes of the EEG net 14 are used to record brain activity of the subject 12 from the cortical regions of the brain. The environment 10 further includes a magnetic resonance imaging (MRI) system 20. The MRI system 20 acquires brain images to provide (to the computing device 18) high resolution, structural images to enable the identification and/or visualization of the seizure focus.

The MRI scan of the brain is provided to the computing device 18, where the MRI brain image is segmented to identify or delineate head tissue types, including gray matter, white matter, cerebrospinal fluid, scalp, skull, air cavities, and eyeballs. The computing device 18 may render the images on a user interface 22 (e.g., display device or display screen) and/or store the image data at a data repository 24. For instance, the user interface 22 enables a visual representation of the tessellated cortical surface, including an image of the head (or portion thereof) with one or any combination of the dipole patches, dipole patch center(s), dipole patch normal(s), or a cortical source. The user interface 22 may be integral to the computing device 18 or be embodied as a separate device. Similarly, the processing device 16 may be integral to the computing device 18 or be embodied as a separate device. The data repository 24 may include one or more of a picture archiving and communication system (PACS), a radiology information system (RIS), a hospital information system (HIS), an electronic medical record (EMR) database, a surgical navigation system, a server, a computer, and/or other data repository. The computing device 18 may export data corresponding to brain activity from the cortical surface to the MRI space for import to surgical navigation systems, which may enable planning of an optimal ablation trajectory based on retrospective data (e.g. activity within ablated areas, tracts, laser trajectory, patient outcome, etc.) from the same procedure in different subjects. The user interface 22 and/or data repository 24 may be local to the MRI system 20 or remotely located (e.g., separate room, separate building, or separate region) and accessed over a network. In some embodiments, functionality of the computing device 18 may be performed locally (local to the clinical facility), remotely, or at multiple locations (remote and local) according to a distributed processing system, including via a cloud platform.

In some embodiments, a cortical surface tessellation system that implements the corresponding method may include the MRI system 20, EEG net 14, processing device 16, computing device 18, user interface 22, and data repository 24. In some embodiments, the cortical surface tessellation system may include fewer components. For instance, in one embodiment, the cortical surface tessellation system may consist of the computing device 18, or in some embodiments, a non-transitory computer readable storage medium of or associated with the computing device 18, the medium comprising executable code/instructions providing for the functionality of the cortical surface to volume mapping system. In some embodiments, the environment 10 may include additional systems and/or devices, including a computerized tomography (CT) system, which may be used to characterize, for instance, skull bone density, and which may provide images that are registered to the MR images. In some embodiments, an electrode registration system or mobile device may be used to register the electrode positions on the head. For instance, the Geodesic Photogrammetry System (GPS) by Philips may be used for electrode registration. In some embodiments, other types of devices may be used for registration.

In general, a cortical surface tessellation system carries out a process of acquiring MRI data, generating a head model based on the MRI data (e.g., to solve the forward problem), recording EEG data, and then using the head model to solve the inverse problem to locate a source of targeted brain activity (e.g., source of a seizure) based on the EEG data. Based on the located source, brain surgery (which is typically preceded by a preplanning stage) may be used to remove the source of the activity (e.g., seizure). As to the head model generation, the cortical surface tessellation system segments the head tissue (e.g., gray matter, skull, etc.), associates different conductivities with respective tissue classes or types (e.g., using known conductivities from research and/or literature), identifies or extracts the cortical surface from the MRI data with topological correction and tessellation in dipole patches, registers the electrode positions on a subject's head, and computes a lead field matrix to predict how current will flow from the cortex to the scalp (using, for instance, one of finite difference method (FDM), finite element method (FEM), boundary element method (BEM), etc.). For instance, the lead field matrix is used to relate dipole activity to changes in measured scalp EEG potentials, and is defined at least in part by an accurate model of head conductivities based on the MRI data (or in some embodiments, by an atlas model). Certain embodiments of a cortical surface tessellation method are described further below with a focus on the head modeling stage, and in particular, the dipole tessellation process, recognizing that the tessellation process advances the objectives of the overall electrical source imaging process.

Figure 2:
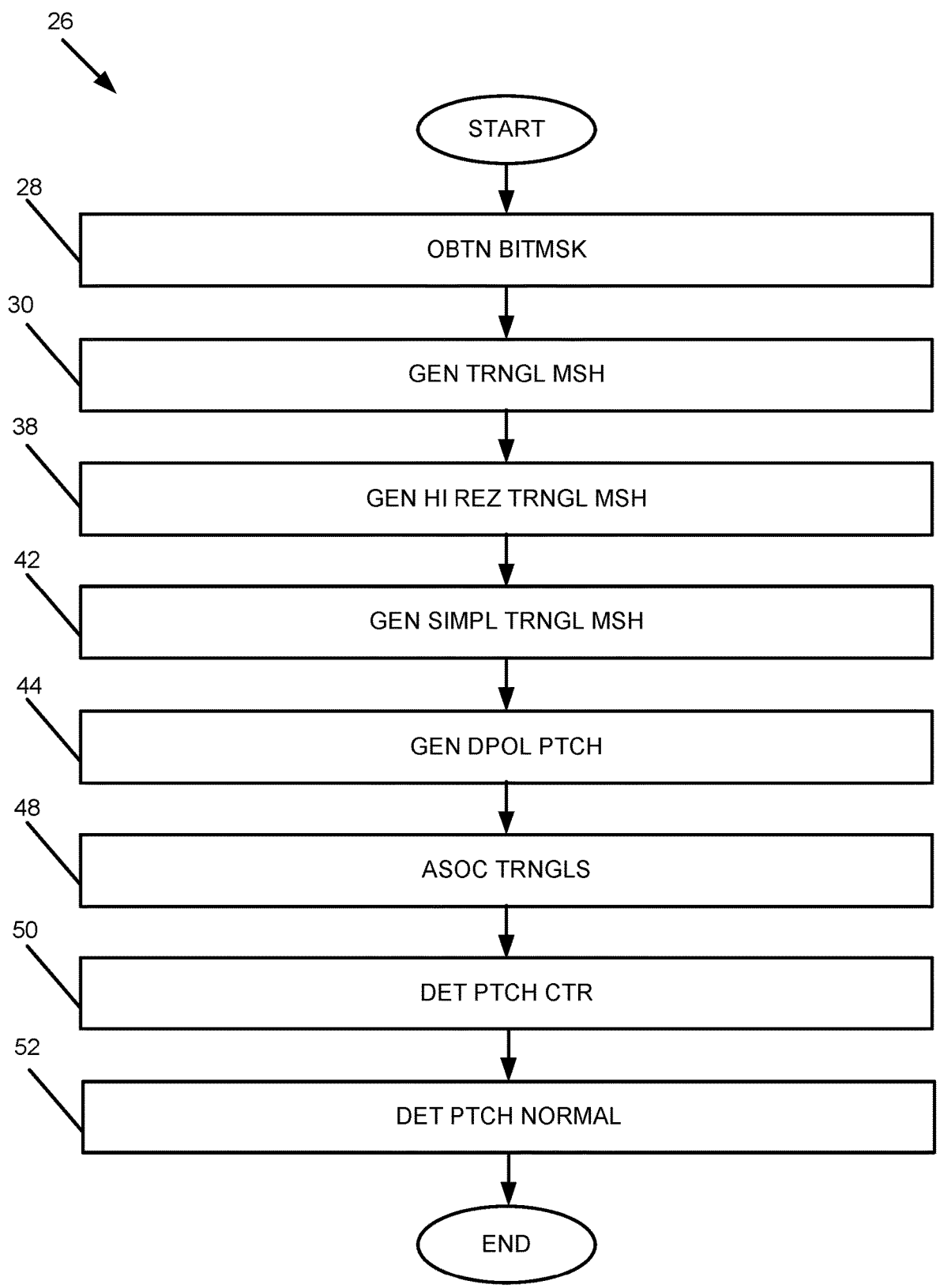
FIG. 2 is a flow diagram that illustrates an example cortical surface tessellation method, in accordance with an embodiment of the invention.

Referring now to FIG. 2, shown is a flow diagram that illustrates an embodiment of an example cortical surface tessellation method 26. Also, reference is made to FIG. 3 in conjunction with the description of FIG. 2, where FIG. 3 conceptually illustrates select functions of the method 26. As explained briefly above, the head modeling process in general begins with receiving a magnetic resonance imaging scan of a subject's head (e.g., from the MRI system 20 (FIG. 1), and the segmentation of the magnetic resonance imaging data, wherein in one embodiment, the segmenting comprises tissue segmentation of a cortical surface of a cortex. For instance, image segmentation software in the computing device 18 (FIG. 1) may access an anatomical model of the brain from an anatomical model bank, the model comprising a surface representation of a shape-constrained deformable brain model. Examples of suitable brain models are described in L. Zagorchev, A. Goshtasby, K. Paulsen, T. McAllister, S. Young, and J. Weese, Manual annotation, 3-D shape reconstruction, and traumatic brain injury analysis, Intl Workshop Multimodal Brain Image Analysis (MBIA), Toronto, Calif., September 2011, and L. Zagorchev, C. Meyer, T. Stehle, R. Kneser, S. Young, and J. Weese, Evaluation of Traumatic Brain Injury patients using a shape-constrained deformable model, Intl Workshop Multimodal Brain Image Analysis (MBIA), Toronto, Calif., September 2011, all of which are incorporated by reference in their entirety. Additional information on shape constrained deformable models may be found in "Shape-constrained deformable models and applications in medical imaging," by Jurgen Weese, Irina Wachter-Stehle, Lyubomir Zagorchev, and Jochen Peters, pages 151-184 of SCDM Book, Chapter 1400, and "Rapid fully automatic segmentation of subcortical brain structures by shape-constrained surface adaptation," Fabian Wenzel, Carsten Meyer, Thomas Stehle, Jochen Peters, Susanne Siemonsen, Christian Thaler, Lyubomir Zagorchev, for the Alzheimer's Disease Neuroimaging Initiative, Medical Image Analysis 46 (2018), pages 141-161, each of which are also incorporated by reference. Other models are also contemplated herein. The image segmentation software is configured to segment the brain based on the anatomy represented in the model by performing an initial registration between the model and the MRI brain image, transforming the model to the brain anatomy based on a transform (e.g., the Hough transform), performing a parametric adaptation of the model, and performing a deformable adaptation of the model. Other known techniques can alternatively be used.

Referring to the cortical surface tessellation method 26 of FIG. 2, the method 26 comprises receiving (obtaining, e.g., from memory or network storage) a volumetric bitmask of the cortex, wherein each voxel is associated with a tissue type (28).

In (30), the method 26 generates (or obtains) a triangular mesh representation of segmented gray matter of the cortex based on the bitmask (e.g., via a marching cubes algorithm). For instance, referring to FIG. 3, a dipole tessellation workflow 32 is shown corresponding to select steps of the method 26, and in particular, a triangular mesh representation based on the bitmask is shown and denoted as triangular mesh representation 34. The cortical bitmask is obtained from a segmentation of an MRI scan and results in dipole patches with normals perpendicular to the dipole surface. The number of generated dipoles is not fixed and depends on the head (cortical) size. The dipole tessellation can be implemented by using a volumetric bitmask of the cortex where each voxel is labelled according to tissue type.

The marching cubes algorithm can be applied to the bitmask to extract a triangular mesh representation of the segmented gray matter representing the cortex. The marching cubes algorithm generates a polygonal representation of constant density surfaces from a three-dimensional array of data, and may generally be described as comprising the following steps: read four slices into memory, scan two slices and create a cube from four neighbors on the next slice, calculate an index for the cube by comparing eight density values at the cube vertices with a surface constant, look up the list of edges from a pre-calculated table using the index, find the surface-edge intersection via linear interpolation using the densities at each edge vertex, calculate a unit normal at each cube vertex using central differences (and interpolate the normal to each triangle vertex), and output the triangle vertices and vertex normal. In effect, the marching cubes algorithm determines how surfaces intersect each cube, then moves or marches to the next cube. Further information on the marching cubes algorithm may be found in the publication entitled, Marching Cubes: A High Resolution 3D Surface Construction Algorithm", William E. Lorensen et al., "Computer Graphics", Volume 21, Number 4, July 1997 (see also SIGGRAPH 1987, pp. 163-169) and the publication, "The Asymptotic Decider: Resolving the Ambiguity in Marching Cubes", Gregory M. Nielson et al., IEEE Visualization 1991: pp. 83-93, all of which are incorporated herein by reference in their entirety. In some embodiments, other surface generation algorithms may be used.

The triangular mesh representation of the cortex obtained by the marching cubes can then be remeshed into a high resolution triangular mesh containing triangles with uniform edge length, and another simplified triangular mesh obtained with a topology preserving mesh decimation algorithm. In other words, the method 26 further comprises generating a higher resolution triangular mesh (see, e.g., higher resolution triangular mesh 36 of FIG. 3) based on the triangular mesh representation, wherein the triangles of the higher resolution triangular mesh have uniform edge lengths (e.g., 1 millimeter edges) (38), and generating a simplified triangular mesh (see, e.g., simplified triangular mesh 40 of FIG. 3) using a mesh decimation algorithm, wherein cortical folding and geometry are maintained (e.g., topology preserving) (42). That is, the simplified mesh is obtained with topology preserving mesh decimation, which maintains the cortical folding and geometry. For instance, the mesh decimation algorithm may be achieved using open-source software that performs 3D computer graphics, image processing, and/or visualization, including a Visualization Toolkit as described in the publication, "Mesh Decimation Using VTK", Knapp, M., 2002, Institute of Computer Graphics and Algorithms, Vienna University of Technology, further edited by Shao Yiyang, "Allen-Shao/Mesh Simplification Wiki—Github", all incorporated herein by reference in their entirety.

Figure 3:
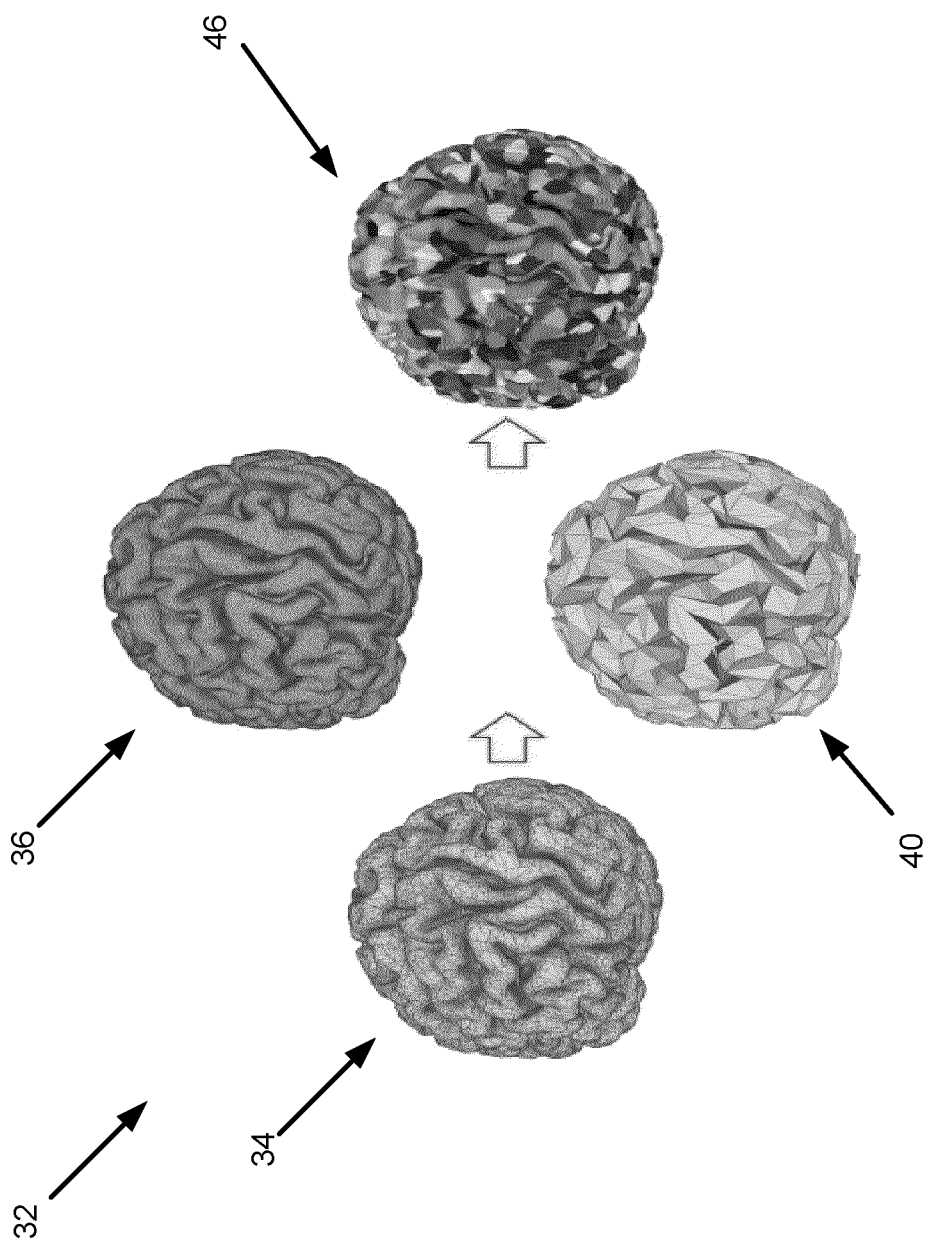
FIG. 3 is a flow diagram that conceptually illustrates an example workflow for select steps of the cortical surface tessellation method of FIG. 2, in accordance with an embodiment of the invention.

In (44), the method 26 further comprises generating dipole patches using the simplified triangular mesh, such as denoted by the cortical dipole patches 46 in FIG. 3. That is, the dipoles patches can be obtained by using the simplified mesh as a template.

In (48), the method 26 associates the triangles in the higher resolution triangular mesh with a closest respective triangle in the simplified triangular mesh. All triangles from the high resolution uniform edge length mesh can be assigned to their closest triangle from the simplified mesh. Thus, the final number of dipole patches equals the number of triangles in the simplified mesh.

In some embodiments, each dipole patch shall have a patch center and a patch normal to define its orientation. In this regard, the method 26 further comprises determining a patch center for each dipole patch (50). In one embodiment, the method 26 determines the patch center by finding a centroid or center of mass of all higher resolution mesh triangles associated with the respective dipole patch (e.g., assigned to that patch) and defining the center of the higher resolution mesh triangle closest to the centroid or center of mass for a particular dipole patch can be selected as the patch center for the respective dipole patch.

In (52), the method 26 further comprises determining a patch normal for each dipole patch by calculating the average of all the higher resolution triangle normals associated with (e.g., assigned to) each respective dipole patch.

The patch normal and/or the patch center and/or tessellation is then used in a model to determine the location of a cortical source based on potentials measured on the scalp of a subject. The resulting dipole patches and patch normals are illustrated in image diagram 54 of FIG. 4.

Note that in some embodiments, variations to the number and/or order of steps or substance of the steps in the method 26 are contemplated to be within the scope of the disclosure.

Figure 5:
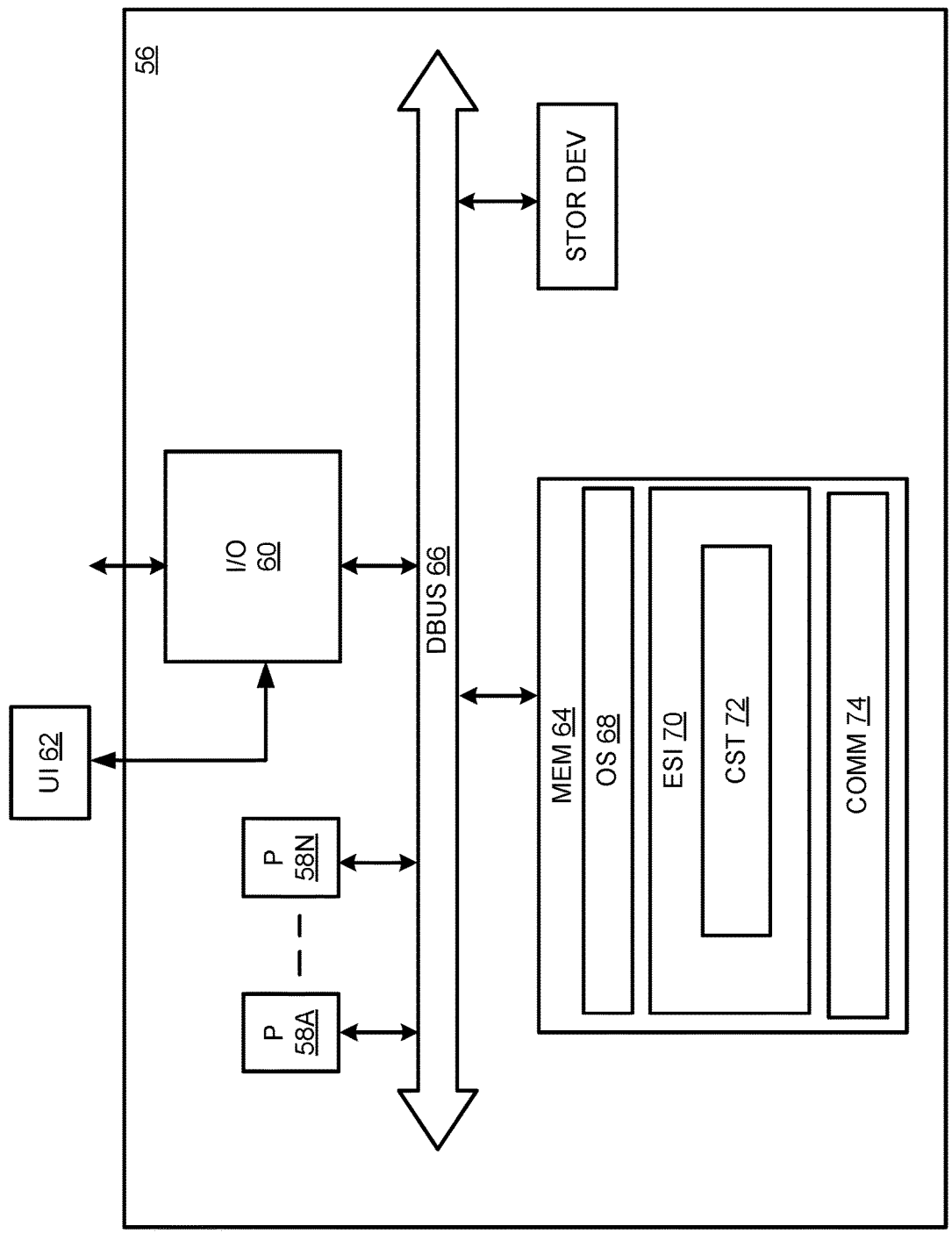
FIG. 5 is a block diagram that illustrates an example apparatus for implementing, all or in part, a cortical surface tessellation method, in accordance with an embodiment of the invention.

Having described an embodiment of a cortical surface tessellation method 26 (FIG. 2), attention is directed to FIG. 5, which illustrates an embodiment of an example apparatus 56 for performing the cortical surface tessellation method 26. The apparatus 56 may be the same or similar to the computing device 18 (FIG. 1). In the depicted embodiment, functionality of a cortical surface tessellation system that performs the method 26 is implemented as an apparatus 56 comprising co-located software and hardware components collectively embodied as a computing device (which may include a medical device, personal computer, tablet, etc.). It should be appreciated that, in some embodiments, the functionality of the cortical surface tessellation system may be performed in one or more devices that reside local to a clinic, imaging machine or system or that reside remote from the imaging machine/system (e.g., in a cloud-based platform, server farm, web servers, application server, etc.). In some embodiments, plural devices remote from each other (e.g., client-server relationship) may collectively perform the functionality of the cortical surface tessellation system in distributed processing fashion. One having ordinary skill in the art should appreciate in the context of the present disclosure that the example apparatus, hereinafter referred to as computing device 56, is merely illustrative of one embodiment, and that some embodiments of computing devices may comprise fewer or additional components, and/or some of the functionality associated with the various components depicted in FIG. 5 may be combined, or further distributed among additional modules or computing devices, in some embodiments. It should be appreciated that certain well-known components of computer systems are omitted here to avoid obfuscating relevant features of the computing device 56.

In one embodiment, the computing device 56 comprises one or more processors 58 (e.g., 58A . . . 58N), input/output (I/O) interface(s) 60, one or more user interfaces 62, which may include one or more of a keyboard, mouse, microphone, speaker, display, etc.), and memory 64, all coupled to one or more data busses, such as data bus 66. In some embodiments, the user interfaces 62 may be coupled directly to the data bus 66. The user interfaces 62 may include the user interface 22 (FIG. 1). The memory 64 may include any one or a combination of volatile memory elements (e.g., random-access memory RAM, such as DRAM, and SRAM, etc.) and nonvolatile memory elements (e.g., ROM, Flash, solid state, EPROM, EEPROM, hard drive, tape, CDROM, etc.). The memory 64 may store a native operating system, one or more native applications, emulation systems, or emulated applications for any of a variety of operating systems and/or emulated hardware platforms, emulated operating systems, etc. In some embodiments, a separate storage device (STOR DEV) may be coupled to the data bus 66 or as a network-connected device (or devices) via the I/O interfaces 60 and one or more networks. In some embodiments, the storage device may serve as the data repository 24 (FIG. 1). In the depicted embodiment, the computing device 56 may be coupled to an imaging system (e.g., MRI system 20) and processing device 16 (FIG. 1) via the I/O interfaces 60, though it should be appreciated that the connection may be achieved via one or more networks in some embodiments or according to other known connections or interconnections. The storage device may be embodied as persistent memory (e.g., optical, magnetic, and/or semiconductor memory and associated drives). In some embodiments, the storage device or memory 64 may store a model bank, one or more bitmasks, scans, meshes, among other subject information. The memory 64 and/or storage device may each be considered as a non-transitory computer-readable storage medium.

In the embodiment depicted in FIG. 5, the memory 64 comprises an operating system 68 (e.g., LINUX, macOS, Windows, etc.), and electrical source imaging (ESI) software 70, which includes functionality for performing electrical source imaging and supporting functions. In one embodiment, the ESI software 70 includes cortical surface tessellation software 72. The cortical surface tessellation software 72 includes one or more modules (executable code or generally, instructions) corresponding to the functionality of the method 26 depicted in, and described in association with, the cortical surface tessellation method 26 (FIG. 2). That is, functionality of the cortical surface tessellation software 72 has been described in conjunction with the cortical surface tessellation method 26 illustrated in FIG. 2, and hence description of the same is omitted here for brevity. Note that reference to software may include software, firmware, middleware, and/or microcode or microinstructions. In some embodiments, functionality of the software may be implemented via hardware (e.g., circuitry, including application-specific integrated circuits (ASICs), field programmable gate arrays (FPGAs), vector processors, tensor processing units, etc.). The memory 64 further comprises a communications module 74. The communications module 74 comprises software that is configured to enable the communication of information (via the I/O interfaces 60) among other systems and/or devices (e.g., of the environment 10, FIG. 1).

Execution of cortical surface tessellation software 72 (and the ESI software 70) may be implemented by the one or more processors 58 under the management and/or control of the operating system 68. The processor(s) 58 may be embodied as a custom-made or commercially available processor, including a single or multi-core central processing unit (CPU), tensor processing unit (TPU), graphics processing unit (GPU), vector processing unit (VPU), or an auxiliary processor among several processors, a semiconductor based microprocessor (in the form of a microchip), a macroprocessor, one or more application specific integrated circuits (ASICs), field programmable gate arrays (FPGUs), a plurality of suitably configured digital logic gates, and/or other known electrical configurations comprising discrete elements both individually and in various combinations to coordinate the overall operation of the computing device 56.

The I/O interfaces 60 comprise hardware and/or software to provide one or more interfaces to other systems or devices, including the data repository 24 (FIG. 1). The I/O interfaces 60 may include a cable, wireless, and/or cellular modem, and/or establish communications with other devices or systems via an Ethernet connection, hybrid/fiber coaxial (HFC), copper cabling (e.g., digital subscriber line (DSL), asymmetric DSL, etc.), using one or more of various communication protocols (e.g., TCP/IP, UDP, etc.). In general, the I/O interfaces 60, in cooperation with the communications module 74 comprises suitable hardware to enable communication of information via PSTN (Public Switched Telephone Networks), POTS, Integrated Services Digital Network (ISDN), Ethernet, Fiber, DSL/ADSL, Wi-Fi, cellular (e.g., 3G, 4G, 5G, Global System for Mobile Communications (GSM), General Packet Radio Service (GPRS), etc.), Bluetooth, near field communications (NFC), Zigbee, among others, using TCP/IP, UDP, HTTP, DSL.

Figure 4:
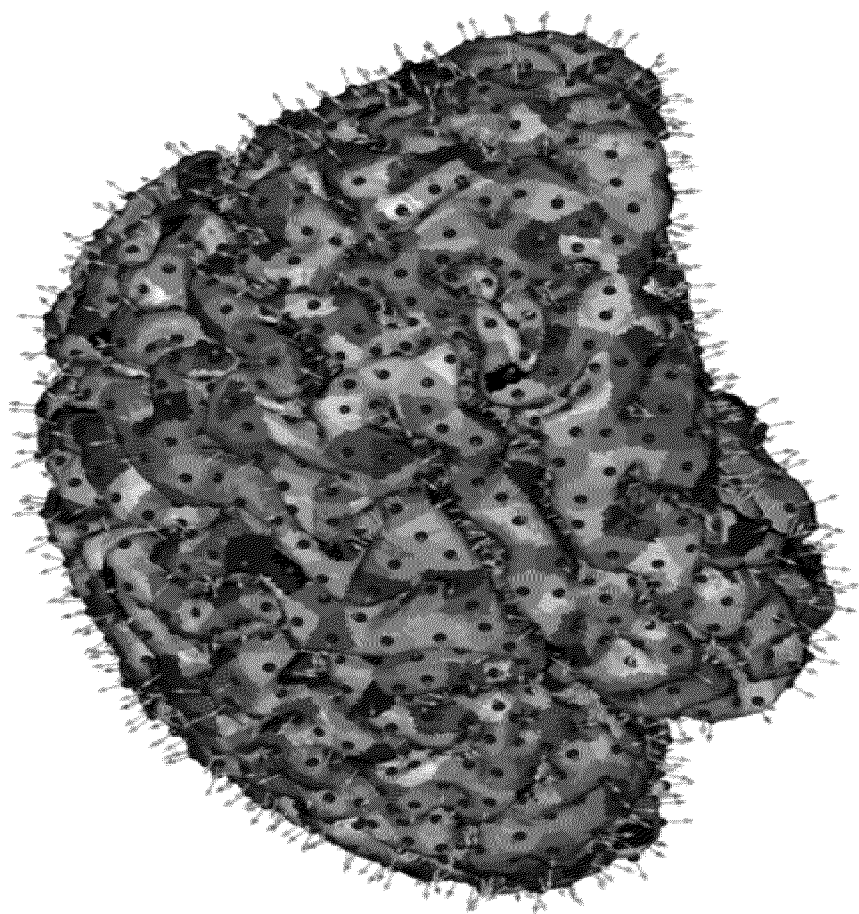
FIG. 4 is an image diagram of an example cortical surface comprising dipole patches and patch normals resulting from implementation of a cortical surface tessellation method, in accordance with an embodiment of the invention.

The user interfaces 62 may include a keyboard, mouse, microphone, display, immersive head set, etc., which enable input and/or output by a clinician, technician, or other user. For instance, the user interfaces 62 may visually represent the results obtained by the method 26 (e.g., location of a patch center, patch normal, such as shown in FIG. 4, and/or visually represent one or more cortical sources. In some embodiments, the user interface 62 may be integrated in the computing device 56, and in some embodiments, coupled to the computing device 56 over one or more wired and/or wireless networks. In some embodiments, the user interfaces 62 may cooperate with associated software to enable augmented reality or virtual reality, or visualization may be achieved in connection with other devices via the I/O interfaces 60.

When certain embodiments of the computing device 56 are implemented at least in part with software (including firmware, middleware, microcode, etc.), it should be noted that the cortical surface tessellation software 72 (and the ESI software 70) can be stored on any one of a variety of non-transitory computer-readable (storage) medium for use by, or in connection with, a variety of computer-related systems or methods. In the context of this document, a computer-readable storage medium may comprise an electronic, magnetic, optical, or other physical device or apparatus that may contain or store a computer program (e.g., executable code or instructions) for use by or in connection with a computer-related system or method. The software may be embedded in a variety of computer-readable storage mediums for use by, or in connection with, an instruction execution system, apparatus, or device, such as a computer-based system, processor-containing system, or other system that can fetch the instructions from the instruction execution system, apparatus, or device and execute the instructions.

When certain embodiments of the computing device 56 are implemented at least in part with hardware, such functionality may be implemented with any or a combination of the following technologies, which are all well-known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), TPUs, GPUs, and/or other accelerators/co-processors, etc.

Figure 6:
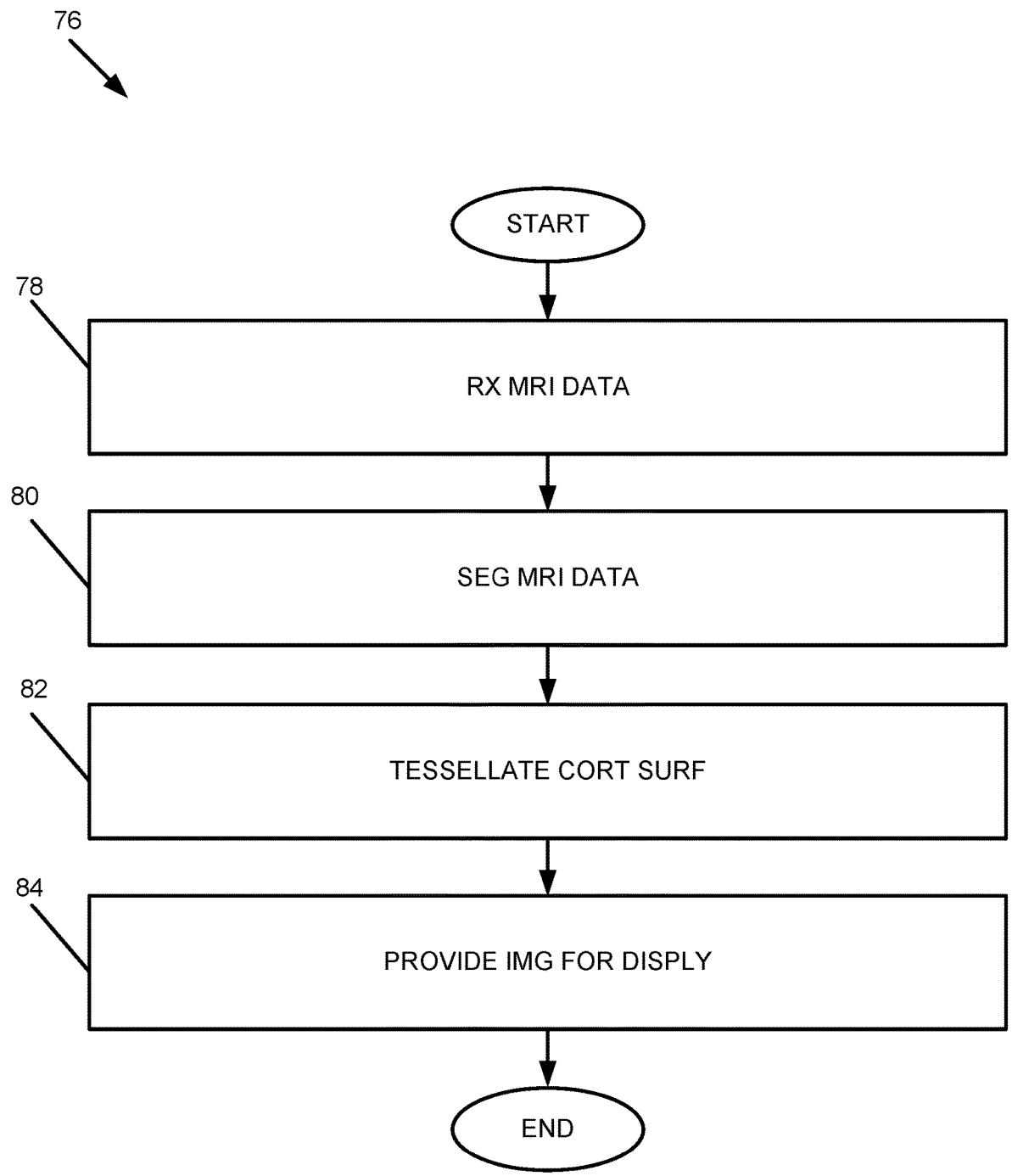
FIG. 6 is a flow diagram that illustrates an example cortical surface tessellation method, in accordance with an embodiment of the invention.

In view of the above description, it should be appreciated that one embodiment of an example cortical surface tessellation method, depicted in FIG. 6 and denoted as method 76, which is shown bounded by a start and end, comprises receiving magnetic resonance imaging data (78); segmenting the magnetic resonance imaging data, the segmenting comprising tissue segmentation of a cortical surface of a cortex (80); tessellating the segmented cortical surface with a plurality of dipole patches, wherein a quantity of the plurality of dipole patches is variable and dependent upon a head size (82); and providing, for display, an image of a head or portion thereof according to the tessellation (84).

Note that the methods 26 (FIG. 2) and 76 may be implemented by the apparatus 56, or by plural devices in some embodiments.

Any process descriptions or blocks in flow diagrams should be understood as representing modules, segments, or portions of code which include one or more executable instructions for implementing specific logical functions or steps in the process, and alternate implementations are included within the scope of the embodiments in which functions may be executed out of order from that shown or discussed, including substantially concurrently or in reverse order, depending on the functionality involved, as would be understood by those reasonably skilled in the art of the present disclosure. In some embodiments, one or more steps may be omitted, or further steps may be added.

The cortical surface tessellation method, apparatus, and system embodiments described herein may improve the accuracy of electrical source imaging in a clinically feasible way, which ultimately may lead to more accurate and patient specific diagnosis and better outcomes.

In one embodiment, a method is disclosed, comprising: receiving magnetic resonance imaging data; segmenting the magnetic resonance imaging data, the segmenting comprising tissue segmentation of a cortical surface of a cortex; tessellating the segmented cortical surface with a plurality of dipole patches, wherein a quantity of the plurality of dipole patches is variable and dependent upon a head size; and providing, for display, an image of a head or a portion thereof according to the tessellation.

In one embodiment, the preceding method, wherein the cortical surface consists of a gray matter surface of the cortex.

In one embodiment, any one of the preceding methods, further comprising: receiving a volumetric bitmask of the cortex, wherein each voxel of a plurality of voxels is labeled according to a tissue type; providing a triangular mesh representation of the segmented cortical surface based on the volumetric bitmask; providing a high resolution triangular mesh containing triangles with uniform edge length by re-meshing the triangular mesh representation; and providing a simplified triangular mesh representation by applying a topology preserving, mesh decimation algorithm to the high resolution triangular mesh representation.

In one embodiment, any one of the preceding methods, wherein the triangular mesh representation of the segmented cortical surface is based on application of a marching cubes algorithm to the bitmask.

In one embodiment, any one of the preceding methods, wherein the topology preserving, mesh decimation algorithm preserves cortical folding and geometry of the segmented cortex.

In one embodiment, any one of the preceding methods, further comprising obtaining the plurality of dipole patches by: associating each triangle from the high resolution triangular mesh representation to its closest triangle from the simplified triangular mesh representation, wherein a final quantity of the plurality of dipole patches equals a quantity of triangles of the simplified triangular mesh representation.

In one embodiment, any one of the preceding methods, wherein each of the plurality of dipole patches comprises properties that are used as boundary conditions in a forward model used in electrical source imaging.

In one embodiment, any one of the preceding methods, wherein the properties include a patch center, a patch normal, and surface triangles associated with each of the plurality of dipole patches.

In one embodiment, any one of the preceding methods, wherein each dipole patch center is determined by: determining a center of mass of all triangles of the high resolution triangular mesh representation associated with a particular one of the closest triangles, wherein a center of a high resolution mesh triangle closest to the center of mass is selected as the dipole patch center; wherein a normal of the dipole patch corresponds to an average of all normals of the triangles of the high resolution triangular mesh representation.

In one embodiment, any one of the preceding methods, further comprising: registering electrode positons on the head; predicting electrical activity of the head based on the tessellated image; recording electroencephalography signals from the head; and based on the recording, predicting a source of targeted brain activity.

In one embodiment, any one of the preceding methods, further comprising displaying the image of the head or the portion thereof according to the tessellation, where the displayed image further comprises a visual representation of one or any combination of a patch center, a patch normal, or a cortical source.

In one embodiment, an apparatus is disclosed, comprising: a memory comprising instructions; and one or more processors configured by the instructions to implement functionality corresponding to any one of the preceding methods.

In one embodiment, a system is disclosed comprising the preceding apparatus, and further comprising: a magnetic resonance imaging system configured to scan a head of the subject and provide the magnetic resonance imaging data to the one or more processors of the apparatus; a plurality of electroencephalography electrodes configured to sense the electroencephalography signals; wherein the one or more processors of the apparatus are configured to receive the electroencephalography signals measured by the electroencephalography electrodes positioned on a scalp of a subject.

In one embodiment, the preceding system, further comprising a display device coupled to the apparatus, the display device configured to display the image of the head or the portion thereof according to the tessellation.

In one embodiment, any one of the preceding systems, where the displayed image further comprises a visual representation of one or any combination of a patch center, a patch normal, or a cortical source.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. Note that various combinations of the disclosed embodiments may be used, and hence reference to an embodiment or one embodiment is not meant to exclude features from that embodiment from use with features from other embodiments. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical medium or solid-state medium supplied together with or as part of other hardware, but may also be distributed in other forms. Any reference signs in the claims should be not construed as limiting the scope.

At least the following is claimed:

1. A method, comprising:
receiving magnetic resonance imaging data;
segmenting the magnetic resonance imaging data, the segmenting comprising tissue segmentation of a cortical surface of a cortex;
tessellating the segmented cortical surface with a plurality of dipole patches, wherein a quantity of the plurality of dipole patches is variable and dependent upon a head size;
receiving a volumetric bitmask of the cortex, wherein each voxel of a plurality of voxels is labeled according to a tissue type;
providing a triangular mesh representation of the segmented cortical surface based on the volumetric bitmask; and
providing, for display, an image of a head or a portion thereof according to the tessellation.

2. The method of the claim 1, wherein the cortical surface consists of a gray matter surface of the cortex.

3. A non-transitory computer readable medium including instructions that when executed by one or more processors cause the one or more processors to perform the method of claim 2.

4. The method of claim 1, further comprising:
providing a high resolution triangular mesh containing triangles with uniform edge length by re-meshing the triangular mesh representation; and
providing a simplified triangular mesh representation by applying a topology preserving, mesh decimation algorithm to the high resolution triangular mesh representation.

5. The method of claim 4, wherein the topology preserving, mesh decimation algorithm preserves cortical folding and geometry of the segmented cortex.

6. The method of claim 4, further comprising obtaining the plurality of dipole patches by:
associating each triangle from the high resolution triangular mesh representation to its closest triangle from the simplified triangular mesh representation, wherein a final quantity of the plurality of dipole patches equals a quantity of triangles of the simplified triangular mesh representation.

7. The method of claim 4, wherein each dipole patch center is determined by:
determining a center of mass of all triangles of the high resolution triangular mesh representation associated with a particular one of the closest triangles, wherein a center of a high resolution mesh triangle closest to the center of mass is selected as the dipole patch center;
wherein a normal of the dipole patch corresponds to an average of all normals of the triangles of the high resolution triangular mesh representation.

8. A non-transitory computer readable medium including instructions that when executed by one or more processors cause the one or more processors to perform the method of claim 4.

9. The method of claim 1, wherein the triangular mesh representation of the segmented cortical surface is based on application of a marching cubes algorithm to the bitmask.

10. The method of claim 1, wherein each of the plurality of dipole patches comprises properties that are used as boundary conditions in a forward model used in electrical source imaging.

11. The method of claim 1, wherein the properties include a patch center, a patch normal, and surface triangles associated with each of the plurality of dipole patches.

12. The method of claim 1, further comprising:
registering electrode positions on the head;
predicting electrical activity of the head based on the tessellated image;
recording electroencephalography signals from the head; and
based on the recording, predicting a source of targeted brain activity.

13. The method of claim 1, further comprising displaying the image of the head or the portion thereof according to the tessellation, where the displayed image further comprises a visual representation of one or any combination of a patch center, a patch normal, or a cortical source.

14. A non-transitory computer readable medium including instructions that when executed by one or more processors cause the one or more processors to perform the method of claim 1.

15. An apparatus, comprising:
a memory comprising instructions; and
one or more processors that, when the one or more processors execute the instructions, are caused to:
receive magnetic resonance imaging data;
segment the magnetic resonance imaging data, the segmenting comprising tissue segmentation of a cortical surface of a cortex;
tessellate the segmented cortical surface with a plurality of dipole patches, wherein a quantity of the plurality of dipole patches is variable and dependent upon a head size;
provide a triangular mesh representation of the segmented cortical surface based on a volumetric bitmask of the cortex, wherein the volumetric bitmask includes a plurality of voxels labeled according to a tissue type; and
provide, for display, an image of a head or a portion thereof according to the tessellation.

16. A system comprising the apparatus of claim 15, and further comprising:
a magnetic resonance imaging system configured to scan a head of the subject and provide the magnetic resonance imaging data to the one or more processors of the apparatus;
a plurality of electroencephalography electrodes configured to sense the electroencephalography signals;
wherein the one or more processors of the apparatus are configured to receive the electroencephalography signals measured by the electroencephalography electrodes positioned on a scalp of a subject.

17. The system of claim 16, further comprising a display device coupled to the apparatus, the display device configured to display the image of the head or the portion thereof according to the tessellation.

18. The system of claim 17, where the displayed image further comprises a visual representation of one or any combination of a patch center, a patch normal, or a cortical source.

19. The apparatus of claim 15, wherein the instructions further cause the one or more processors to receive the volumetric bitmask of the cortex.

20. The apparatus of claim 15, wherein the instructions further cause the one or more processors to:
- provide a high resolution triangular mesh containing triangles with uniform edge length by re-meshing the triangular mesh representation; and
- provide a simplified triangular mesh representation by applying a topology preserving, mesh decimation algorithm to the high resolution triangular mesh representation.

\* \* \* \* \*